United States Patent [19]

Kelman

[11] Patent Number: 4,769,035

[45] Date of Patent: Sep. 6, 1988

[54] ARTIFICIAL LENS AND THE METHOD FOR IMPLANTING SUCH LENS

[76] Inventor: Charles D. Kelman, 260 Grand Central Pkwy., Floral Park, N.Y. 11005

[21] Appl. No.: 57,287

[22] Filed: Jun. 2, 1987

[51] Int. Cl.$^4$ .............................................. A61F 2/16
[52] U.S. Cl. ...................................................... 623/6
[58] Field of Search ........................................... 623/6

[56] References Cited

U.S. PATENT DOCUMENTS 4,585,456  4/1986  Blackmore .............................. 623/6

FOREIGN PATENT DOCUMENTS 3439551  4/1986  Fed. Rep. of Germany .......... 623/6
0118985  9/1984  European Pat. Off. ................ 623/6
1103399  5/1955  France ..................................... 623/6

Primary Examiner—Ronald L. Frinks
Attorney, Agent, or Firm—Henry Sternberg; Bert J. Lewen

[57] ABSTRACT

An artificial lens adapted for implantation in the human eye and the method for implanting such lens. The lens is of pliable material so that it may be folded or curled for insertion through a minimum length incision. It has a medial optic portion having a posterior concave surface corresponding to the anterior surface of the natural lens when the latter is in its flattest natural condition, and haptic portions for seating the lens in the eye such that the posterior concave surface of the medial optic portion of the artificial lens seats directly against the anterior surface of the natural lens of the eye which remains in and is not removed from the eye. The method according to the invention includes determining the shape of the anterior surface of the natural lens when the latter is in its flattest natural condition, forming the posterior surface of the optic of the artificial lens such as to correspond substantially to that shape and seating the lens in the posterior chamber between the iris and the natural lens with the posterior concave surface of the artificial lens seated on the anterior convex surface of the natural lens.

12 Claims, 1 Drawing Sheet

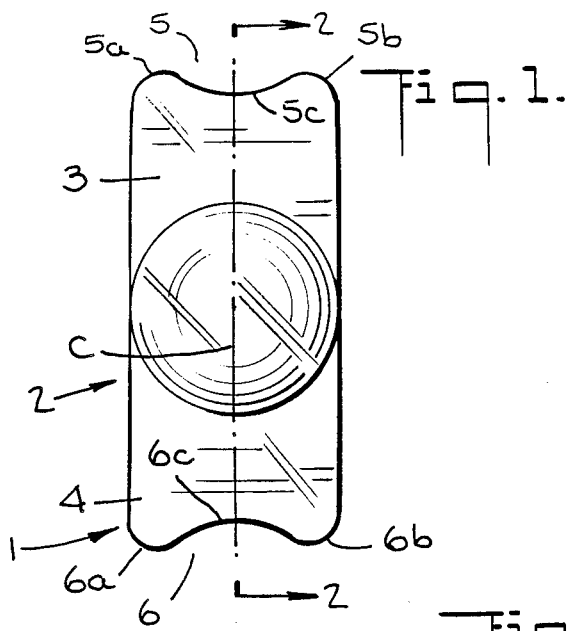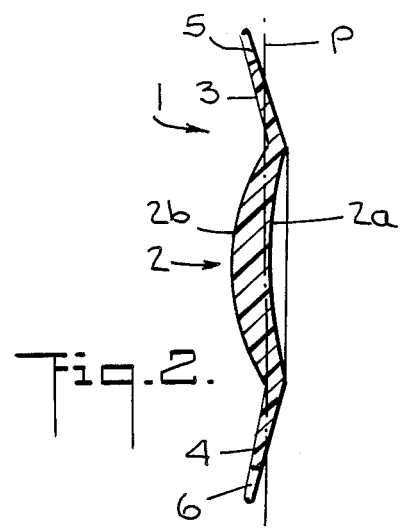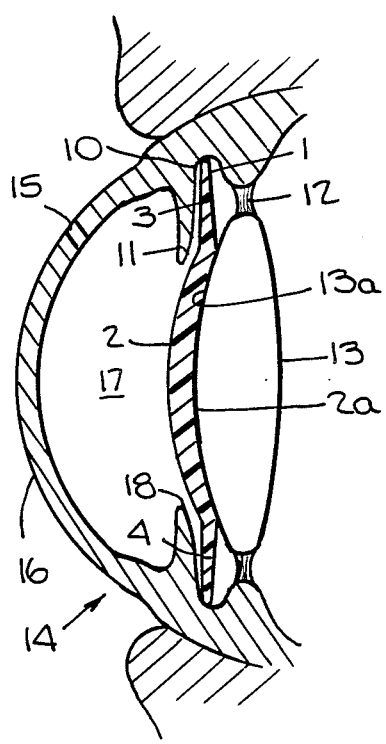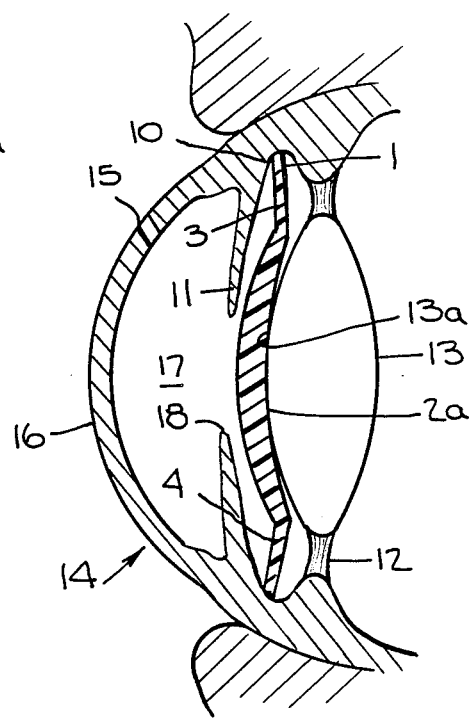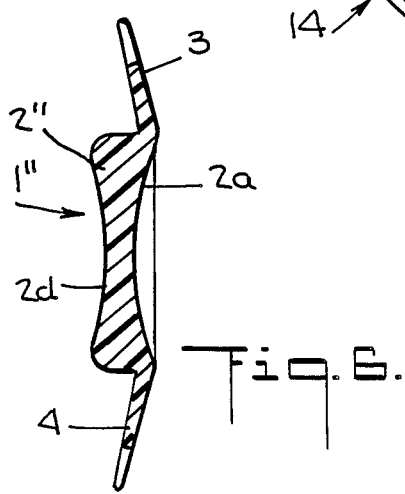

ARTIFICIAL LENS AND THE METHOD FOR IMPLANTING SUCH LENS

FIELD AND BACKGROUND OF THE INVENTION

The present invention relates to an artificial lens and the method for implanting such lens in the eye to cooperate with the natural lens for correcting the eyesight of the eye in question.

The natural lens in the human eye is deformable and attached at its periphery by zonules which allow the biconvex natural lens to be deformed from a first condition in which the lens is flattest (i.e., non-accommodating), to a second condition in which the natural lens is more convex than in said first condition. Thus, the normal, healthy natural lens can conform to the optical power which is required.

In those cases where the natural lens does not properly accommodate to achieve the desired vision, or in other cases where the length of the eyeball is such that the image from a healthy lens falls short or behind the retina, spectacles or contact lenses are required to compensate for the deficiency of the natural lens or axial length. Such external devices are cumbersome, particularly in cases of high degree of myopia where the external lenses have to be quite thick in order to adequately compensate.

Spectacles have the disadvantages that they are often uncomfortable to wear, can fall off and break and are frequently perceived as marring the appearance of the wearer. Contact lenses, on the other hand, cannot be tolerated by everyone and even those who can tolerate such lenses face well known problems associated therewith. For example, the necessity to maintain the lenses absolutely clean, difficulties in removing and inserting the lenses, occasional unpleasant irritation as a result of wearing the contact lenses, possible infection and, on occasion, losing a lens.

SUMMARY OF THE INVENTION

It is among the objects of the present invention to provide a surgical procedure for correcting myopia or hyperopia.

It is another object of the present invention to provide such a surgical procedure which does not involve either removal of the natural lens or reshaping of the cornea.

It is a further object of the present invention to provide such a procedure which will be readily adoptable by surgeons who are experienced with procedures for implantation of intraocular lenses.

It is a still further object of the present invention to provide a lens implant for use with such procedure.

It is a concomitant object of the present invention to provide such lens implant which will cooperate with the natural lens to correct the eyesight of the eye in question.

According to one embodiment of the invention there is provided a surgical procedure for correcting the eyesight of a human eye, comprising the steps of determining the amount of optical correction required for correcting the eyesight of the eye, determining the shape of the anterior surface of the natural lens in the eye providing an artificial lens having a medial optic portion which has a posterior face of concave shape complementing substantially the shape of the convex anterior surface of the natural lens, when the latter is in its flattest, natural condition in the eye and an anterior face chosen, in relation to the concave curvature of the posterior face, such that the optical power of the resulting optic will provide the amount of optical correction determined for the eye in question, inserting the artificial lens through an incision in the eye, and seating the artificial lens in the eye, with the optic portion located between the iris and the natural lens of the eye and with the posterior surface of the optic portion of the artificial lens in substantial face-to-face apposition (separated by a thin layer of aqueous humor) with the anterior surface of the natural lens and in substantial optical alignment therewith.

According to another embodiment of the invention there is provided an artificial lens implant for correcting the eyesight of a human eye, comprising a medial optic portion exhibiting the optical power required for correcting the eyesight of the eye in question, and, seating means extending from said medial optic portion, for seating the lens in the eye in such position that said medial optic portion is located between the iris and the natural lens in the eye, said optic portion having a posterior face of concave shape corresponding in curvature substantially to the curvature of the anterior face of the natural lens in the eye in which said artificial lens is to be implanted and having a anterior face of such shape that the combined effect of said anterior and posterior faces of said optic portion is to provide the appropriate optical power required for correcting the eyesight of the eye in question.

Thus, a lens implant is provided which may be inserted into the eye through a relatively small incision and will thereafter readily correct myopia of varying degree, including high degrees of myopia. By varying the shape of the anterior surface of the implant, such implant and the procedure described above can also be used to correct hyperopia.

BRIEF DESCRIPTION OF THE DRAWINGS

Other and further objects and advantages of the present invention will become apparent from the within specification and accompanying drawings, in which:

FIG. 1 is a enlarged front elevational view of the intraocular lens according to one embodiment of the present invention;

FIG. 2 is a cross-sectional view taken along the line 2—2 of FIG. 1;

FIG. 3 is a enlarged schematic cross-sectional partial view of a human eye showing the intraocular lens of FIGS. 1 and 2 seated therein, with the pupil dilated and the natural lens in its flattest condition thereof;

FIG. 4 is a enlarged schematic cross-sectional partial view of a human eye showing the intraocular lens of FIGS. 1 and 2 seated therein, with the pupil contracted and the natural lens in its most convex condition;

FIG. 5 is a enlarged cross-sectional view of a lens according to another embodiment of the present invention; and FIG. 6 is a enlarged cross-sectional view of a lens according to still another embodiment of the present invention.

DESCRIPTION OF THE PREFERRED EMBODIMENTS

Referring to the drawings, and initially to FIGS. 1 and 2, an intraocular lens according to one embodiment of the present invention is shown, which is usable for implantation in the human eye between the iris and the natural lens in the eye, without removing the natural lens.

Lens 1 comprises a central optic portion 2 and a pair of preferably generally flat haptic portions 8 and 4 extending in opposite directions from opposite peripheral portions of the optic 2. The haptic portions 3, 4 have distal seating portions 5 and 6, respectively, each having a pair of spaced rounded seating projections 5a, 5b and 6a, 6b, respectively, separated preferably by intermediate concave portions 5c and 6c, respectively.

Preferably, the flat haptic portions 3 and 4 are slightly inclined, as best seen in FIG. 2, with respect to a central plane P of the optic portion 2. Such inclination may be approximately of the order of 10 or 15 degrees. The rounded seating projections 5a, 5b and 6a, 6b are preferably formed so as to provide minimum contact surface with the eye tissue which the lens contacts when seated, and the aforesaid angle of inclination is preferably chosen such as to maintain the intraocular lens seated on the natural lens, as will be explained below, after the haptics 3 and 4 of the intraocular lens are seated in the eye.

Optic portion 2 is formed with a concave posterior surface 2a and preferably has a convex anterior surface 2b, as best seen in FIG. 2. It will be noted, however, that the optic portion 2 may be, according to another embodiment of the present invention, formed with a planar anterior surface 2c, such as seen in FIG. 5, or a concave anterior surface 2d, as, for example, the embodiment illustrated in FIG. 6.

In each instance, however, the concave configuration of the posterior surface will be such as to correspond substantially to the anterior surface of the natural lens in the eye when the latter is in its flattest, i.e., non-accommodating condition. Thus, as may be seen in FIG. 3, the lens 1 according to one embodiment of the present invention is seated in the ciliary sulcus 10 formed between the iris 11 and the zonules 12 which support the natural lens 13 of the eye 14. Preferably, the lens 1 according to the invention is formed of silicone or other similarly pliable material and may be folded, for example, along its longitudinal center line C, seen in FIG. 1, or may be curled generally about said longitudinal center line, for forming a cylinder no more than about 3 mm in diameter, and approximately 13 mm in length (representing the longitudinal length of the lens 1). Optic 2 is preferably about 6 mm in diameter and has a maximum thickness, i.e., measured along the optical axis, of about 2 mm. The haptics 3 and 4 preferably have a width of about 6 mm and a thickness of about 1 mm. Inasmuch as the entire lens is formed of pliable material and because of the concave shape of the posterior surface 2a thereof and the relatively thin haptics, the lens 1 may be readily folded or curled along its longitudinal center line C into, for example, the aforesaid cylindrical shape which will fit through a minimum length incision 15 in the cornea 16 of the eye. Such incision need not be longer than 3 mm, to thereby minimize trauma associated with such surgery.

Preferably, according to the method of the present invention, a visco-elastic substance, such as Healon (registered trademark) is used to temporarily maintain the anterior chamber 17 in expanded condition. At such time, the artificial lens according to this invention is inserted, in curled or folded condition, through the incision 15, into the anterior chamber and the inferior portion of lens 1 is passed through the pupil 18 and seated behind the iris 11 in the inferior portion of groove 10 formed between the iris and the zonules supporting the natural lens 13, which remains in the eye. Thereafter, the superior portion of the artificial lens is passed through the pupil 18 and seated in the superior portion of the same groove 10. Consequently, the artificial lens 1 will be positioned between the iris 11 and the natural lens 13, with the posterior concave surface 2a of the optic 2, in substantial surface-to-surface contact with the anterior surface 13a of the natural lens 13.

Prior to such insertion and seating, the desired shape of the concave posterior surface 2a of lens 1 is determined by measuring the shape of convex anterior surface 13a of the natural lens of the eye to determine the exact configuration thereof. Such determination may be made by means well-known to those skilled in the art as, for example, the use of ultra-sonography, using a "B" scan or an "A" scan. Once that determination is made, the surgeon will either choose, from an inventory of lenses, that lens which has a posterior concave surface configuration most closely resembling the mirror image of the convex anterior surface of the natural lens, or will have a lens ground, or otherwise formed, to the desired configuration. Such configuration will be determined with the natural lens in its flattest, i.e., non-accommodating, condition. The anterior surface of the optic of the artificial lens will be formed to such configuration as will correct the eyesight desired to be corrected. This determination will be based on a measurement of the corrective power of the natural lens in the eye and determining the curvature of the anterior surface of the optic of the artificial lens which, when cooperating with the natural lens, will provide the proper corrective power for the eye in question. Preferably, the seating of the artificial lens 1 on the natural lens 13 is such that surfaces 2a and 13a will be in substantial surface to surface contact with one another without a space therebetween, at least when the natural lens 13 is in its flattest, i.e., non-accommodating, condition. As previously noted, the inclination of the haptic portions 3 and 4 is such that the optic 2 will be urged thereby toward and into such seating engagement with the surface 13a of the natural lens.

FIG. 4 illustrates the relationship between the artificial lens 1 and the natural lens 13 after the natural lens has assumed its most convex condition. It will be seen that in this condition of the natural lens only the central portion of the concave posterior surface of the optic 2 remains in seating contact with the surface 13a, while the peripheral portions of the concave posterior surface of the optic may be slightly spaced from the natural lens due to the more convex shape of natural lens surface 13a. Still, however, the arrangement is such that, even in this condition, the iris, (shown in FIG. 4 with the pupil contracted) will be able to function normally without substantial impediment. In this connection, it should be noted that it has been found that eyes exhibiting a high degree of myopia, for example, are usually enlarged and have somewhat enlarged spaces between the elements thereof, such as between the natural lens and the iris so as to provide sufficient room for the optic 2 to be positioned therebetween.

It will be seen that while the lens 1 of FIGS. 1 thru 4, is particularly suitable for correcting the eyesight of persons suffering from myopia, including those suffering from a high degree of myopia, the lens according to the embodiment generally illustrated in FIG. 6 is capable of correcting the eyesight of persons suffering from hyperopia. Thus, the plano-concave optic of the FIG. 5 embodiment and the concavo-concave optic of the FIG. 6 embodiment, represent variations of the lens according to the present invention. In each case, however, the optic will have a concave posterior surface for seating engagement with the anterior surface of the natural lens of the eye.

It will be understood, of course, that any means may be employed to measure the shape of the convex anterior surface of the natural lens in the eye and similarly that any one of many well known means may be used to measure the optical power required for correcting the eyesight of the eye in question. Those skilled in the art are familiar with apparatus and techniques for making these measurements.

It will also be understood that the lens according to the present invention, while preferably formed of a single piece of silicone or similarly pliable material, may have its central optic portion formed of one such material and its haptic portions formed of another material suitably connected thereto. It will also be understood that the haptic portions need not be of the specific shape shown and described herein and that other haptics, for example, individual strands or loops, as are well known to those skilled in the art, may be conveniently used.

It will be appreciated that the foregoing specification and accompanying drawings set forth, by way of illustration and not limitation, the present invention and that various modifications and changes may be made therein without departing from the spirit and scope of the present invention which is to be limited solely by the scope of the appended claims.

What is claimed is:

1. A surgical procedure for correcting the eyesight of a human eye, comprising:
    determining the amount of optical correction required for correcting the eye sight of the eye,
    determining the shape of the anterior surface of the natural lens in the eye when the latter is in its flattest natural condition,
    providing an artificial lens having a medial optic portion of pliable material and a pair of seating portions extending from the medial optic portion,
    forming the posterior surface of the optic portion of such lens with a concave shape substantially conforming in curvature to the convex shape determined for the anterior surface of the natural lens of the eye when the latter is in its flattest natural condition and forming the anterior surface of the optic portion of the artificial lens such that the combined anterior and posterior surfaces of the artificial lens will provide the predetermined optical power for correcting the eyesight of the eye in question,
    inserting the artificial lens in the eye, including making a relatively small incision in the eye, deforming the artificial lens into a contracted condition thereof and inserting the contracted lens through said relatively small incision, and,
    seating the artificial lens in the eye, including placing one of the seating portions of the lens through the pupil into seating engagement with the corresponding portion of the groove in the posterior chamber of the eye formed between the iris and the zonules supporting the natural lens, seating the posterior surface of the optic portion of the artificial lens in substantial face-to-face contact with the anterior surface of the natural lens and in substantial optical alignment therewith, and seating the other seating portion of the artificial lens in its corresponding portion of the groove formed between the iris and the zonules.

2. An artificial lens implant for correcting the eyesight of a human eye, comprising:
    a medial optic portion of pliable material having a concave posterior face shaped to conform substantially to the convex shape of the anterior surface of the natural lens when the latter is substantially in its flattest natural condition thereof, said concave posterior face of said artificial lens being adapted to seat on and in substantial face-to-face contact with the anterior surface of the natural lens in the eye when the latter is in substantially its flattest natural condition thereof and to remain seated thereon during normal changes of shape of the natural lens, and said optic portion having an anterior face of such shape that the combined effect of said anterior and posterior faces of said optic portion is to provide the appropriate optical power required for correcting the eye sight of the eye in question, and,
    seating means comprising a pair of opposed seating portions extending in generally opposite directions from said medial optic portion, for seating the lens in the eye in such position that said medial optic portion will be seated on the natural lens in the eye, said seating portions of the lens being adapted to seat in opposite grooved portions, respectively, of the eye, formed between the iris and the zonules thereof.

3. The lens according to claim 2 wherein each of said opposed seating portions comprises a pair of spaced outwardly extending contact points for fixating the lens in the eye.

4. The lens according to claim 2, wherein said material of said optic portion is silicone.

5. The lens according to claim 2, wherein said anterior face of said optic portion of said artificial lens is convex.

6. The lens according to claim 2, wherein said anterior face of said optic portion of said artificial lens is planar.

7. The lens according to claim 2, wherein said anterior face of said optic portion of said artificial lens is concave.

8. The lens according to claim 2, wherein said lens is generally rectangular in shape and said seating portions are a pair of sheet portions extending in diametrically opposed directions from said medial optic portion.

9. The lens according to claim 2, wherein said anterior surface of said optic portion is shaped such as to correct severe myopia of the eye in question.

10. The lens according to claim 2, wherein said anterior surface of said optic portion is shaped such as to correct hyperopia of the eye in question.

11. The lens according to claim 2 wherein said optic portion and said seating means are formed of a single piece of silicone and at least said optic portion is optically clear.

12. The lens according to claim 2 wherein said lens is formed of material which is sufficiently pliable to allow said lens to be curled about a longitudinal axis thereof for insertion thru a minimum size incision.

* * * * *